(12) United States Patent (10) Patent No.: US 7,951,184 B2
Schuessler et al. (45) Date of Patent: May 31, 2011

(54) INFLATABLE BLANKET FOR USE IN CARDIAC SURGERY

(75) Inventors: Wayne Schuessler, St. Louis, MO (US); Karin Feit, St. Augustin (DE); Michael Vardanega, Livermore, CA (US); Dennis Chivetta, Ballwin, MO (US); Thomas Kappel, St. Louis, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 995 days.

(21) Appl. No.: 11/654,351

(22) Filed: Jan. 16, 2007

(65) Prior Publication Data

US 2007/0118195 A1 May 24, 2007

Related U.S. Application Data

(62) Division of application No. 10/322,388, filed on Dec. 19, 2002, now Pat. No. 7,172,616.

(60) Provisional application No. 60/348,671, filed on Jan. 17, 2002.

(51) Int. Cl.
 *A61F 7/00* (2006.01)
 *A61F 7/08* (2006.01)
(52) U.S. Cl. ........................... 607/107; 607/104
(58) Field of Classification Search .................. 607/107
 See application file for complete search history.

(56) References Cited

U.S. PATENT DOCUMENTS

| 1,320,967 | A | | 10/1920 | Clairmont |
| 2,512,559 | A | | 6/1950 | Williams |
| 2,930,594 | A | * | 3/1960 | MacCracken ............... 165/284 |
| 3,215,418 | A | * | 11/1965 | Fannon, Jr. ................. 432/147 |
| 3,444,922 | A | | 5/1969 | Dingman |
| 4,094,357 | A | | 6/1978 | Sgroi |
| 4,114,620 | A | | 9/1978 | Moore et al. |
| 4,572,188 | A | | 2/1986 | Augustine et al. |
| 4,628,931 | A | * | 12/1986 | Barrett ........................ 607/96 |
| 4,660,388 | A | | 4/1987 | Greene, Jr. |
| 5,125,238 | A | | 6/1992 | Ragan et al. |
| 5,165,127 | A | | 11/1992 | Nicholson |
| 5,184,612 | A | | 2/1993 | Augustine |
| 5,241,951 | A | * | 9/1993 | Mason et al. ............... 607/104 |
| 5,265,599 | A | * | 11/1993 | Stephenson et al. ......... 607/104 |
| 5,300,100 | A | | 4/1994 | Hickle et al. |
| 5,300,102 | A | * | 4/1994 | Augustine et al. ........... 607/107 |
| 5,304,213 | A | | 4/1994 | Berke et al. |
| 5,318,568 | A | | 6/1994 | Kaufmann et al. |
| 5,324,320 | A | | 6/1994 | Augustine et al. |
| 5,330,519 | A | * | 7/1994 | Mason et al. ............... 607/104 |
| 5,350,417 | A | | 9/1994 | Augustine |
| 5,392,847 | A | | 2/1995 | Stephenson |
| 5,405,370 | A | | 4/1995 | Irani |
| 5,405,371 | A | | 4/1995 | Augustine et al. |
| 5,443,488 | A | | 8/1995 | Namenye et al. |
| 5,545,194 | A | | 8/1996 | Augustine |

(Continued)

*Primary Examiner* — Roy D Gibson
*Assistant Examiner* — Kaitlyn E Helling
(74) *Attorney, Agent, or Firm* — Fletcher Yoder

(57) ABSTRACT

A method of performing cardiac surgery on a patient's heart, including covering a patient with an inflatable blanket for a forced air convection system, the inflatable blanket having at least one separable seal line within the blanket. The separable seal line may be separated to form a slit. A patient's femoral artery is accessed through the slit, and an elongate medical instrument is passed through the slit, and through the femoral artery toward the patient's heart. Cardiac surgery is performed with the elongate medical instrument, and the elongate medical instrument is withdrawn from the femoral artery through the slit.

14 Claims, 9 Drawing Sheets

U.S. PATENT DOCUMENTS

| | | |
|---|---|---|
| 5,658,325 A | 8/1997 | Augustine |
| 5,674,269 A | 10/1997 | Augustine |
| 5,683,439 A | 11/1997 | Jensen |
| 5,697,963 A | 12/1997 | Augustine |
| 5,720,774 A | 2/1998 | Glucksman |
| 5,728,145 A | 3/1998 | Phlipot et al. |
| 5,733,318 A | 3/1998 | Augustine |
| 5,735,890 A * | 4/1998 | Kappel et al. .................. 607/104 |
| 5,785,716 A | 7/1998 | Bayron et al. |
| 5,860,292 A | 1/1999 | Augustine et al. |
| 5,890,243 A | 4/1999 | Dickerhoff |
| 5,928,274 A | 7/1999 | Augustine |
| 5,941,907 A | 8/1999 | Augustine |
| 5,964,792 A | 10/1999 | Augustine |
| 5,968,084 A | 10/1999 | Augustine et al. |
| 5,991,666 A | 11/1999 | Vought |
| 6,036,722 A | 3/2000 | Augustine |
| 6,049,927 A | 4/2000 | Thomas et al. |
| 6,102,936 A | 8/2000 | Augustine et al. |
| 6,112,348 A | 9/2000 | Dickerhoff |
| 6,119,474 A | 9/2000 | Augustine et al. |
| 6,126,681 A | 10/2000 | Van Duren et al. |
| 6,149,674 A | 11/2000 | Borders |
| 6,168,612 B1 | 1/2001 | Augustine et al. |
| 6,176,870 B1 | 1/2001 | Augustine |
| 6,203,567 B1 | 3/2001 | Augustine |
| 6,210,428 B1 | 4/2001 | Augustine et al. |
| 6,228,107 B1 | 5/2001 | Arnold et al. |
| 6,290,716 B1 | 9/2001 | Augustine |
| 6,511,501 B1 * | 1/2003 | Augustine et al. .............. 607/96 |

* cited by examiner

US 7,951,184 B2

INFLATABLE BLANKET FOR USE IN CARDIAC SURGERY

CROSS-REFERENCE TO RELATED APPLICATIONS

This application is a division of application Ser. No. 10/322,388 now U.S. Pat. No. 7,172,616, filed Dec. 19, 2002, which claims the benefit of Provisional Application Ser. No. 60/348,671, filed Jan. 17, 2002.

BACKGROUND OF THE INVENTION

1. Field of the Invention

The invention relates to inflatable blankets for use with patients.

2. Description of the Related Art

Certain heart surgeries such as angioplasty involve inserting a catheter or other elongate medical instrument into the femoral artery of a patient's thigh, and passing the elongate medical instrument through the blood vessels to the heart.

Excessive cooling of the patient is undesirable during surgery. Various patient warming systems have been proposed, including forced-air warming blankets that bathe a patient with warm air. However, known forced-air warming blankets for covering a patient's lower body interfere with access to the patient's thigh, necessary for performing cardiac surgery through the femoral artery.

Forced-air warming blankets operate by use of a hose connected to the blanket for inflating the blanket with warm air. Positioning of the air delivery hose in forced-air warming blankets can interfere with performing cardiac surgery through the femoral artery.

It also is desirable to provide a disposable forced-air warming blanket as a sterile unit. However, unwrapping and positioning of the blanket over a patient can compromise a sterile field established around a patient.

Additionally, the air delivery hose for inflating a forced-air warming blanket is not likely to be sterile. Connecting and operating an unsterile air delivery hose with a forced-air warming blanket can thus also compromise the sterile field established around a patient.

There thus remains a need in the art for improved forced-air warming blankets for use in cardiac surgery.

SUMMARY OF THE INVENTION

In accordance with the present invention, cardiac surgery is performed on a patient utilizing an inflatable blanket for a forced-air convection system. The invention involves covering a patient with an inflatable blanket for a forced air convection system, the inflatable blanket having at least one separable seal line within the blanket, which separable seal line may be separated to form a slit; accessing a patient's leg (e.g. femoral) artery through the slit; passing an elongate medical instrument through the slit, and through the femoral artery toward the patient's heart; performing cardiac surgery with the elongate medical instrument; and withdrawing the elongate medical instrument from the femoral artery through the slit.

According to one embodiment, the inflatable blanket comprises an upper sheet of material; a lower sheet of material, at least a portion of which is air-permeable; wherein said upper sheet and said lower sheet are sealed together around peripheral edges thereof to form an inflatable blanket having an upper end, a lower end for positioning near feet of a patient when said blanket is in use, and two sides which may be, e.g. substantially parallel, with an inflatable cavity between the upper and lower sheets, an inflation port located at the lower end of the inflatable blanket connecting said inflatable cavity with the atmosphere and through which air may be introduced to said inflatable cavity to inflate said blanket; and wherein said upper sheet and said lower sheet are further sealed together along at least two separable seal lines, such that when at least one of said separable seal lines is separated to form a slit, access through the blanket is provided through said slit to a desired area of the patient on whom said blanket is being utilized, wherein said separable seal lines are located in an upper half of said blanket opposite said lower end, said separable seal lines are spaced away from and do not intersect said upper end, said sides and said lower end, and said separable seal lines are two sides which may be, e.g. substantially parallel with each other and with said sides of said blanket.

DETAILED DESCRIPTION OF THE PREFERRED EMBODIMENTS

In one embodiment, the invention provides an inflatable blanket for a forced air convection system comprising an upper and a lower sheet of material, with at least a portion of the lower sheet being air-permeable. The upper and lower sheets are sealed together around their peripheral edges to form an inflatable blanket, preferably having a generally rectangular shape with an upper end, a lower end for positioning near the feet of a patient when the blanket is in use, and two sides which may be, e.g. substantially parallel, with an inflatable cavity between the upper and lower sheets. An inflation port may be located at the lower end of the inflatable blanket to connect the inflatable cavity with the atmosphere and through which an inflation medium may be introduced to the inflatable cavity to inflate the blanket. The upper and lower sheets are further sealed together along at least two separable seal lines, such that when the separable seal lines are separated to form slits, access to desired areas of the patient on whom the blanket is being utilized is provided through the blanket through the slits. The slits of the seal lines are located in an upper half of the blanket opposite the lower end, the slits are spaced away from and do not intersect the upper end, the sides and the lower end, and the slits are substantially parallel with each other and with the sides of the blanket.

In another embodiment, the invention provides a method of using the inflatable blanket described above which includes the steps of tearing open a pouch containing the blanket in a folded condition, removing the blanket from the pouch, placing the blanket in the folded condition over a patient, opening the blanket down and out, attaching a hose of the blanket to a source of an inflation medium, extending a shield over the hose, and inflating the blanket.

Figure 1:
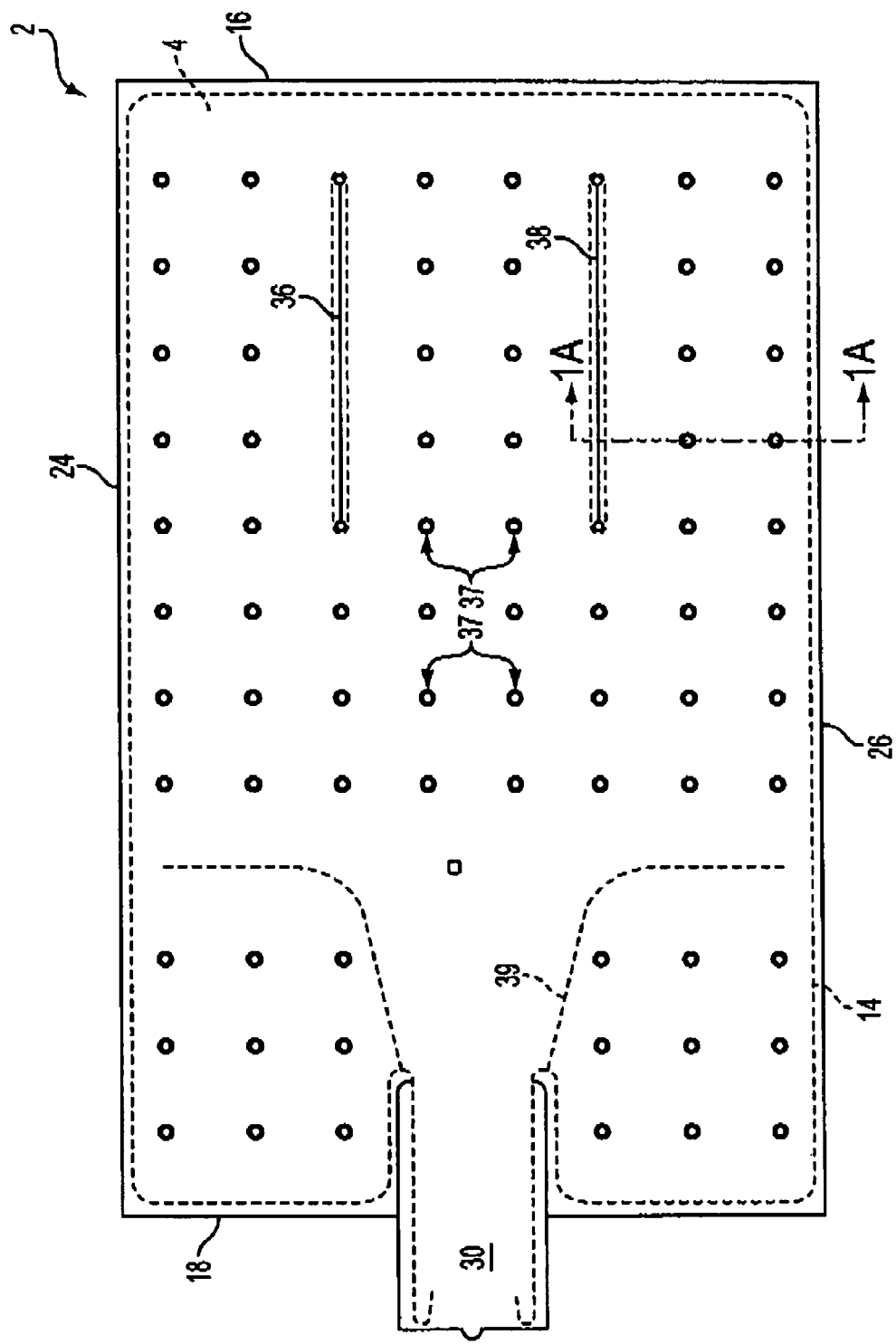
FIG. 1 shows a plan view of an inflatable blanket for a forced air convection system according to one embodiment of the invention.

In FIG. 1 is shown an inflatable blanket 2 for a forced air convection system according to a first embodiment of the invention. The inflatable blanket 2 includes an upper sheet 4 and a lower sheet (not shown in FIG. 1). Inflatable blanket 2 may be made of, e.g. a polymer such as a plastic, a fabric, or a composite fiber.

Inflatable blanket 2 has a generally rectangular shape with an upper end 16, a lower end 18 for positioning near, e.g. feet of a patient when the blanket 2 is in use, and two sides 24, 26 which may be, e.g. substantially parallel, with an inflatable cavity between the upper sheet 4 and the lower sheet.

The upper sheet 4 and the lower sheet are sealed together around peripheral edges 14 to form the inflatable blanket 2. Peripheral edges 14 may be sealed by, e.g. plastic welding, heat welding, or by applying an adhesive to one or both peripheral edges 14 and matching peripheral edges 14 together. The adhesive may be e.g. a two-part adhesive, such as an epoxy.

Upper sheet 4 and the lower sheet may also be sealed together along at least two separable seal lines 36, 38 in a substantially similar manner. Separable seal lines 36, 38 may be formed by, e.g. a line of perforations, or an adhesive or heat or plastic weld between upper sheet 4 and the lower sheet, or within upper sheet 4 and the lower sheet, which is weak in, e.g. shear or tension relative to the local shear or tensile strength of a parent material of inflatable blanket 2.

Upper sheet 4 and the lower sheet may also be sealed together at spot welds 37 and weld lines 39 in a manner substantially similar to that of peripheral edges 14. Weld lines 39 may, e.g. direct an inflation medium flow entering the blanket around the area of a patient's feet, thus limiting the inflation medium flow around the patient's feet. In a preferred embodiment, weld lines 39 end approximately 2 inches or 5.08 centimeters from peripheral edge 14, leaving a gap through which a limited amount of an inflation medium may flow into the area of the blanket 2 proximate to the patient's feet.

Inflatable blanket 2 further includes an inflation port 30 communicating with an inflation cavity. Weld lines 39 may, e.g. form a central air passageway within the inflatable cavity communicating with the inflation port.

Figure 1A:
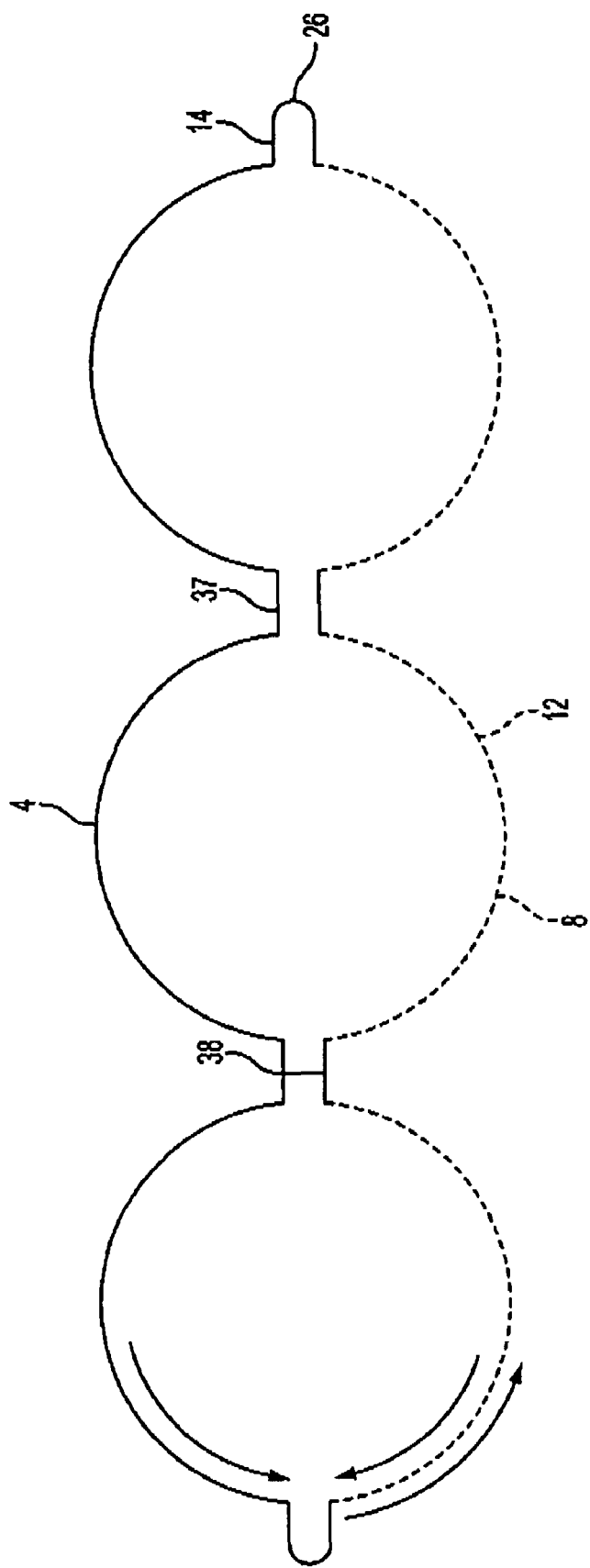
FIG. 1A shows a partial section through the embodiment of the inflatable blanket shown in FIG. 1.

In FIG. 1A is shown a partial section 1A-1A through a spot weld 37 of inflatable blanket 2. In FIG. 1A upper sheet 4 and lower sheet 8 are sealed together at spot welds 37. Lower sheet 8 may be perforated with perforations 12.

Figure 2:
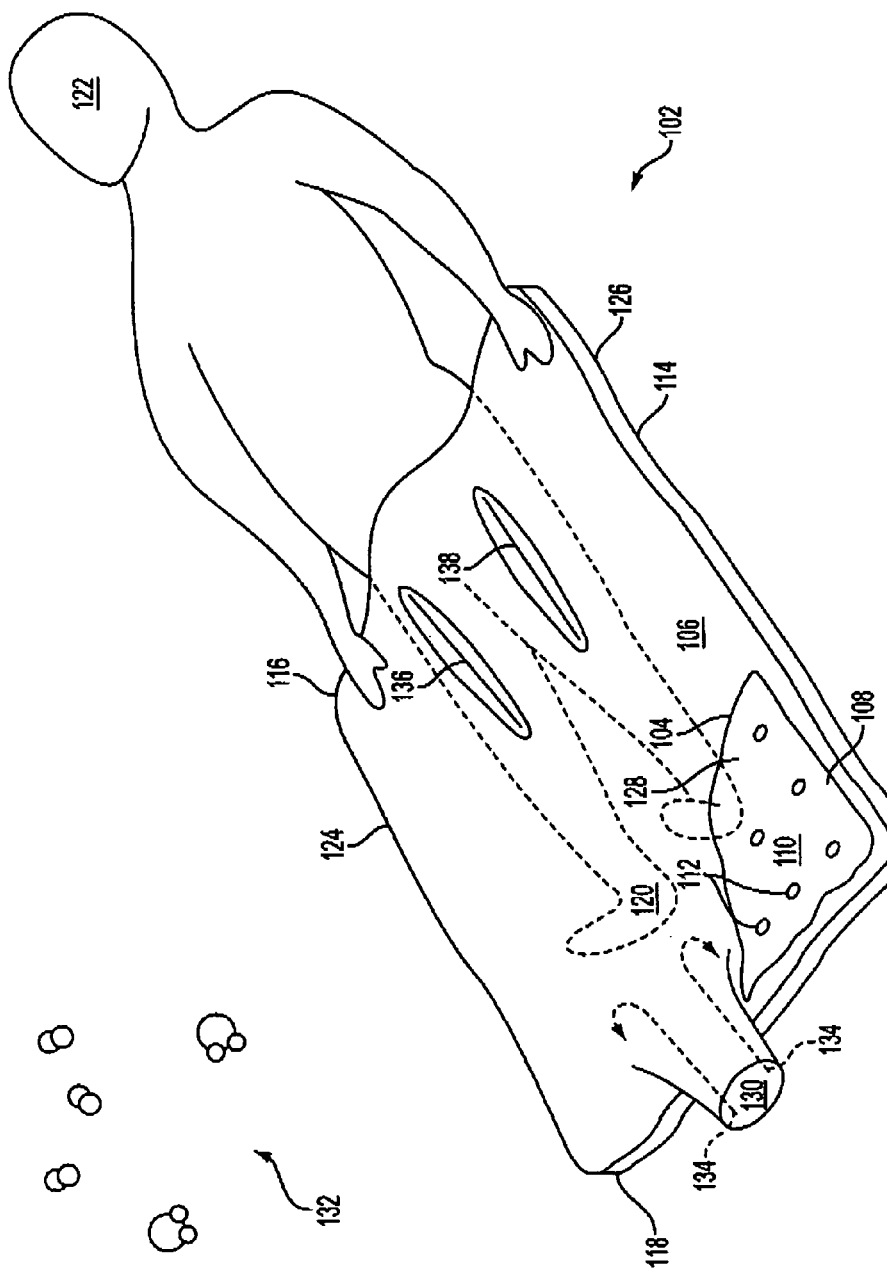
FIG. 2 shows a three-quarter view, partially cut-away, of an inflatable blanket for a forced air convection system according to a second embodiment of the invention.

In FIG. 2 is shown an inflatable blanket 102 for a forced air convection system according to a second embodiment of the invention. The inflatable blanket 102 includes an upper sheet 104 of a first material 106 and a lower sheet 108 of second material 110. First and second materials 106, 108 may be, e.g. a polymer such as a plastic, a fabric, or a composite fiber. First and second materials 106, 108 may be the same material, or different materials.

The upper sheet 104 and lower sheet 108 are sealed together around peripheral edges 114 to form the inflatable blanket 102. Upper and lower sheets 104, 108 may be sealed by, e.g. plastic welding, heat welding, or by applying an adhesive to one or both peripheral edges 114 and matching peripheral edges 114 together. The adhesive may be e.g. a two-part adhesive, such as an epoxy. Upper sheet 104 and lower sheet 108 may also be sealed together along at least two separable seal lines 136, 138 in a substantially similar manner. Separable seal lines 136, 138 may be formed by, e.g. a line of perforations, or an adhesive or heat or plastic weld between upper and lower sheets 104, 108, or within upper and lower sheets 104, 108, which is weak in, e.g. shear or tension relative to the local shear or tensile strength of parent first or second materials 106, 108.

In the illustrated embodiment, inflatable blanket 102 has a generally rectangular shape with an upper end 116, a lower end 118 for positioning near, e.g. feet 120 of a patient 122 when the blanket 102 is in use, and two sides 124, 126 which may be, e.g. substantially parallel, with an inflatable cavity 128 between the upper and lower sheets 104, 108.

An inflation port 130 located at the lower end 118 of the inflatable blanket 102 connects the inflatable cavity 128 with the atmosphere 132 and through which an inflation medium 134 may be introduced to the inflatable cavity 128 to inflate the blanket 102. At least a portion of lower sheet 108 is air-permeable though perforations 112. Perforations 112 may be, e.g., small holes or slits. The size or aggregate flow area of perforations 112 may be, e.g., matched to a rate of flow of inflation medium 134 into blanket 102 such that blanket 102 remains inflated during use, but does not burst.

Inflation medium 134 may be, e.g. air, such as a combination of oxygen, water vapor, nitrogen, and trace elements like argon, or an inert gas such as $N_2$. Inflation medium 134 may be introduced to inflatable cavity 128 by, e.g. pumping inflation medium 134 into inflatable cavity 128, applying a pressure differential across inflatable cavity 128 between inflation port 130 and perforations 112 or any alternative egress, or by evacuating some portion of the surroundings of blanket 102. In a preferred embodiment, inflation medium 134 may be heated. Heat may also, e.g. provide at least some of the pressure differential across inflatable cavity 128 described above.

Figure 3:
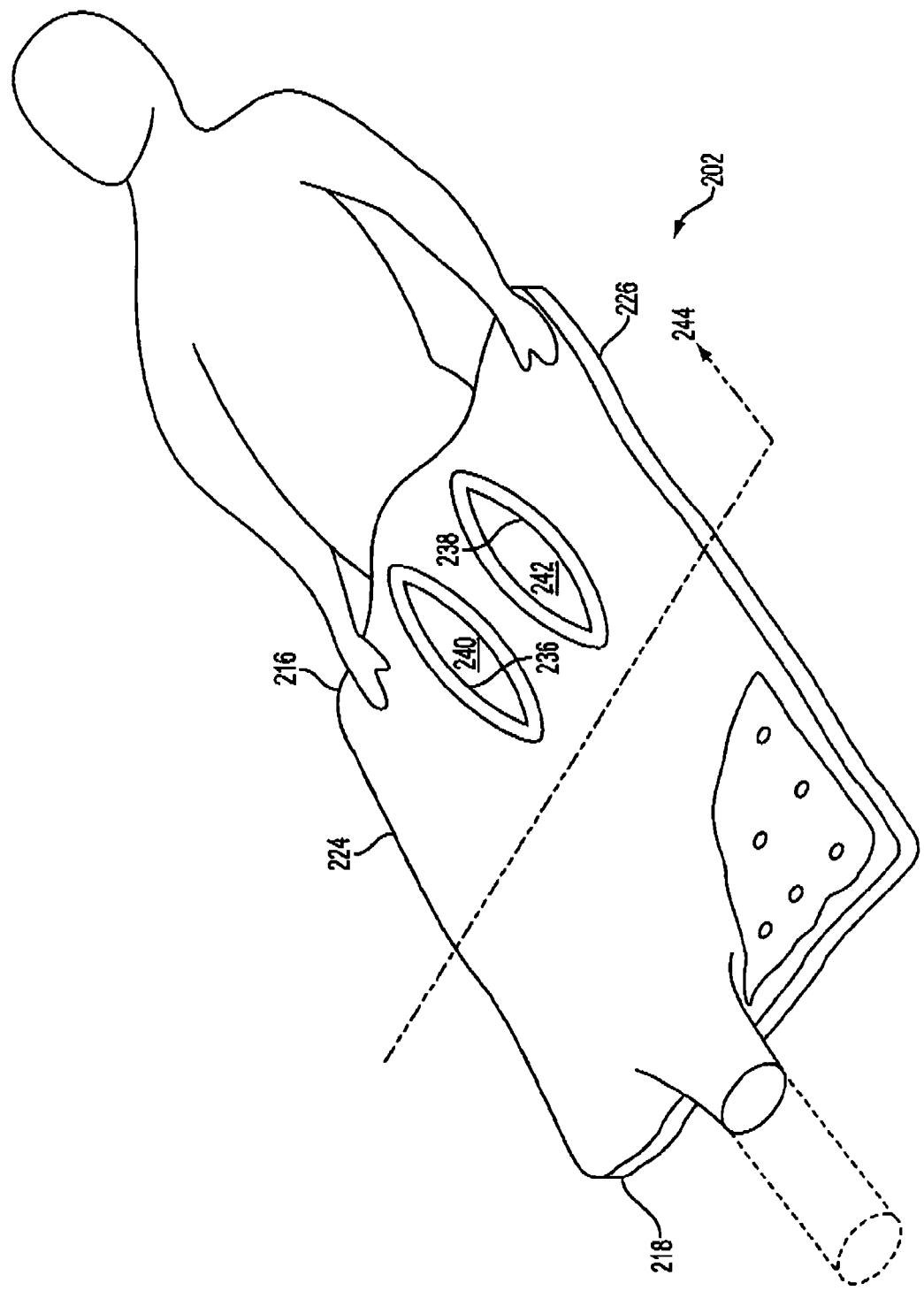
FIG. 3 shows separable seal lines for use with an embodiment of the invention.

As shown in FIG. 3, separable seal lines 236, 238 may be separated to form slits 240, 242 without substantially deflating blanket 202. Access to desired areas of the patient on whom the blanket 202 is being utilized is provided through the slits 240, 242. Slits 240, 242 may, e.g. offer access to the thighs of a patient, after, e.g. a vein harvesting operation. Slits 240, 242 are located in an upper half 244 of the blanket 202 opposite the lower end 218, the slits 240, 242 are spaced away from and do not intersect the upper end 216, the sides 224, 226 or the lower end 218. Slits 240, 242 may be, e.g. substantially parallel with each other and with the sides 224, 226 of the blanket 202. In a preferred embodiment, slits 240, 242 may be tear-open slits.

Figure 4:
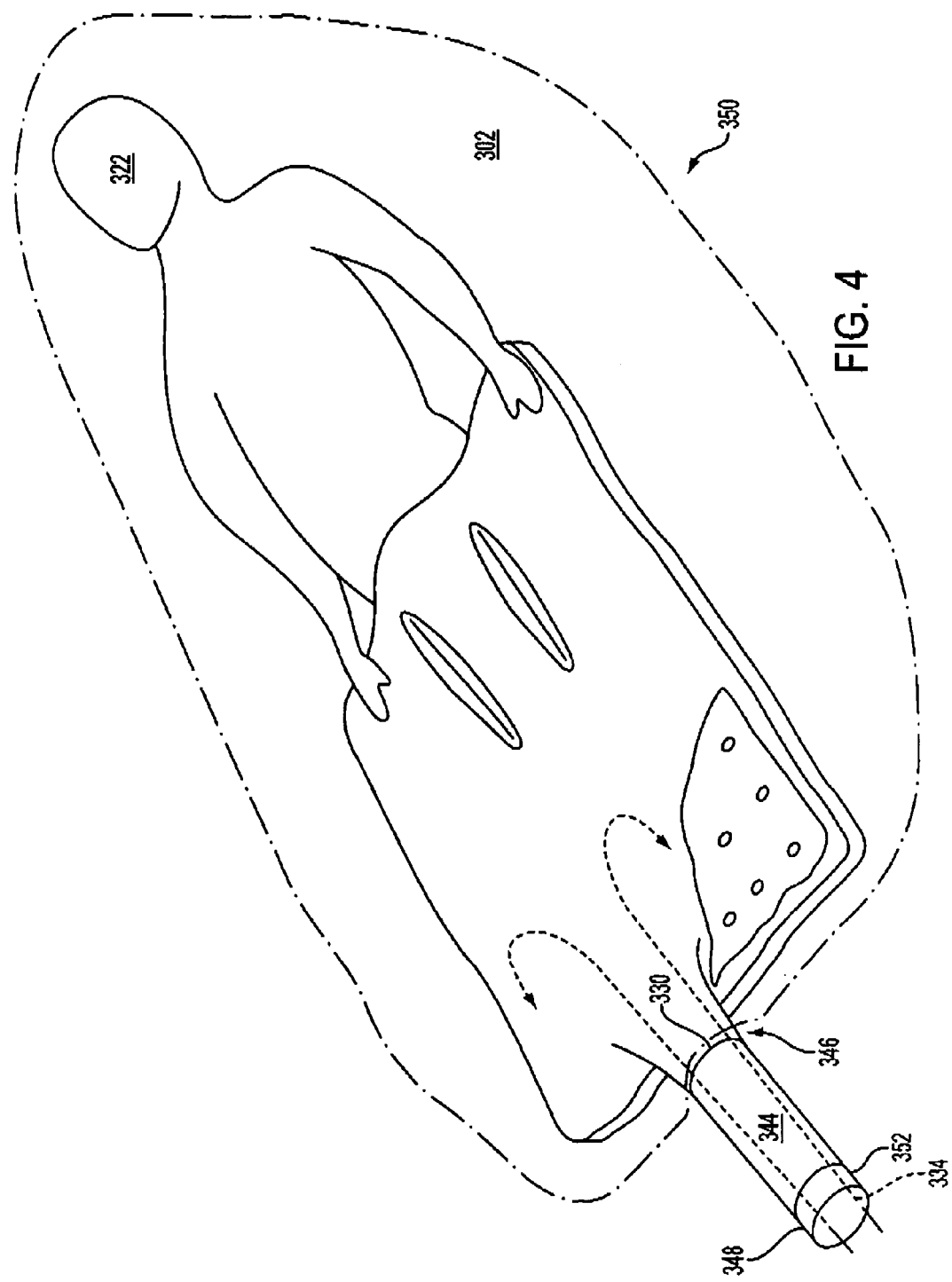
FIG. 4 shows a three-quarter view, partially cut-away, of an inflatable blanket for a forced air convection system according to a third embodiment of the invention.

In a third embodiment of inflatable blanket 302 shown in FIG. 4, a hose 344 with a proximate end 346 may connect the inflation port 330 with a distal end 348 located outside a sterile field 350. Hose 344 may be, e.g. an air supply hose or a plastic tube. Sterile field 350 may be, e.g. an area around patient 322 in which an effort has been made to substantially dispose of, remove, or otherwise render harmless bacteria, organisms, viruses, vileness & corruption, or other entities, living or non-living, that may be potentially detrimental to the health or recovery of patient 322.

Figure 5:
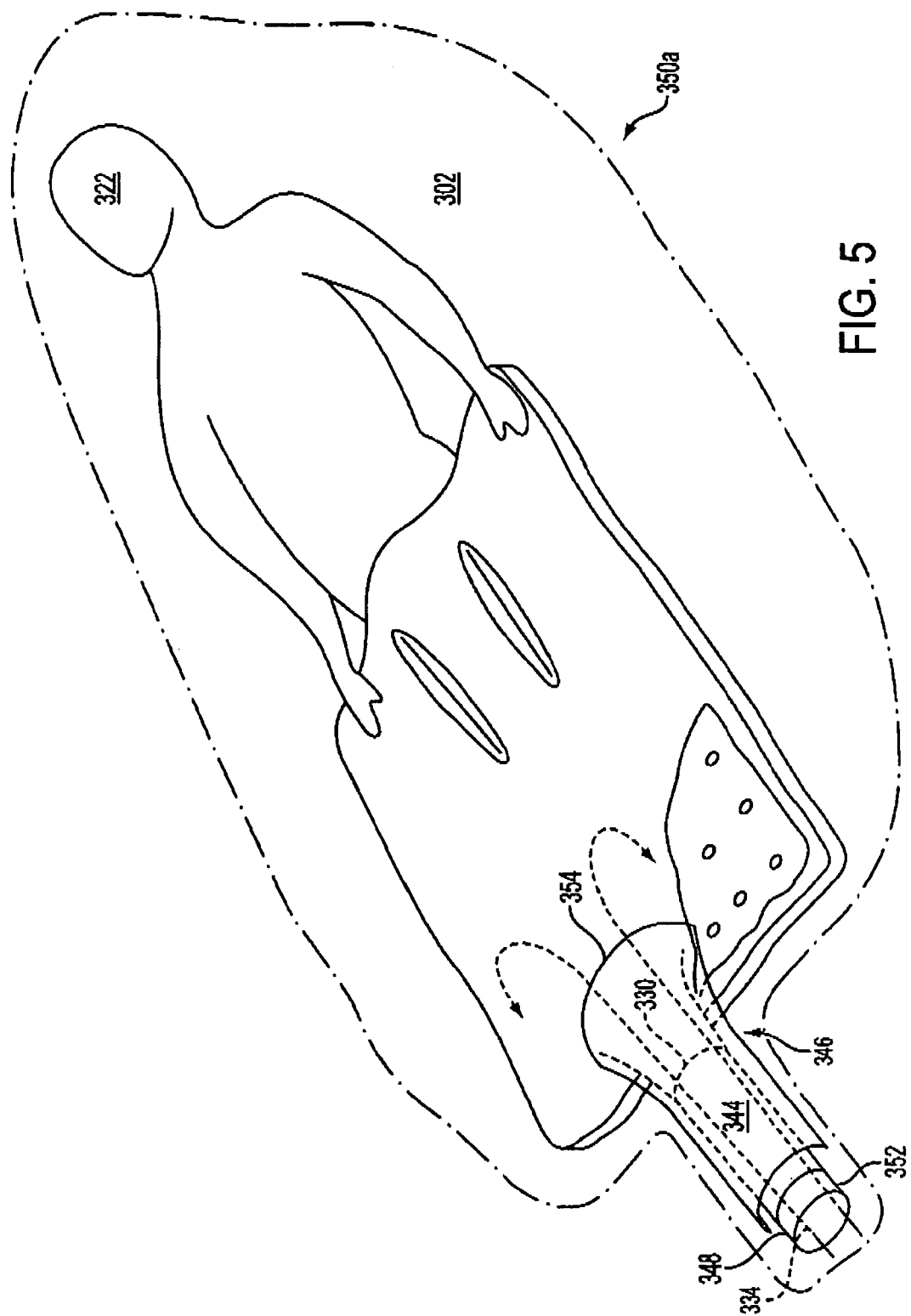
FIG. 5 a three-quarter view, partially cut-away, of a shield for use with the embodiment of the invention shown in FIG. 4.

Inflatable blanket 302 may be inflated through the distal end 348 so that the sterile field 350 is not compromised by the incoming inflation medium 334. Thus, inflation medium 334 may enter hose 344 at distal end 348 and travel through hose 344 to proximate end 344 without substantially contacting or contaminating sterile field 350. In one embodiment, the distal end may have a nozzle 352. Nozzle 352 may be, e.g. a connector of the 'quick disconnect' variety. Nozzle 352 may further comprise a restriction for, e.g. controlling or limiting the rate of flow of inflation medium 334. In a preferred embodiment, shown in FIG. 5, a shield 354 is placed over the nozzle 352 to extend the sterile field 350a over the hose 344. Shield 354 may be, e.g. a tubular or semi-tubular sheath made of, e.g. plastic, rubber, a composite, or a fiber mat.

Figure 6:
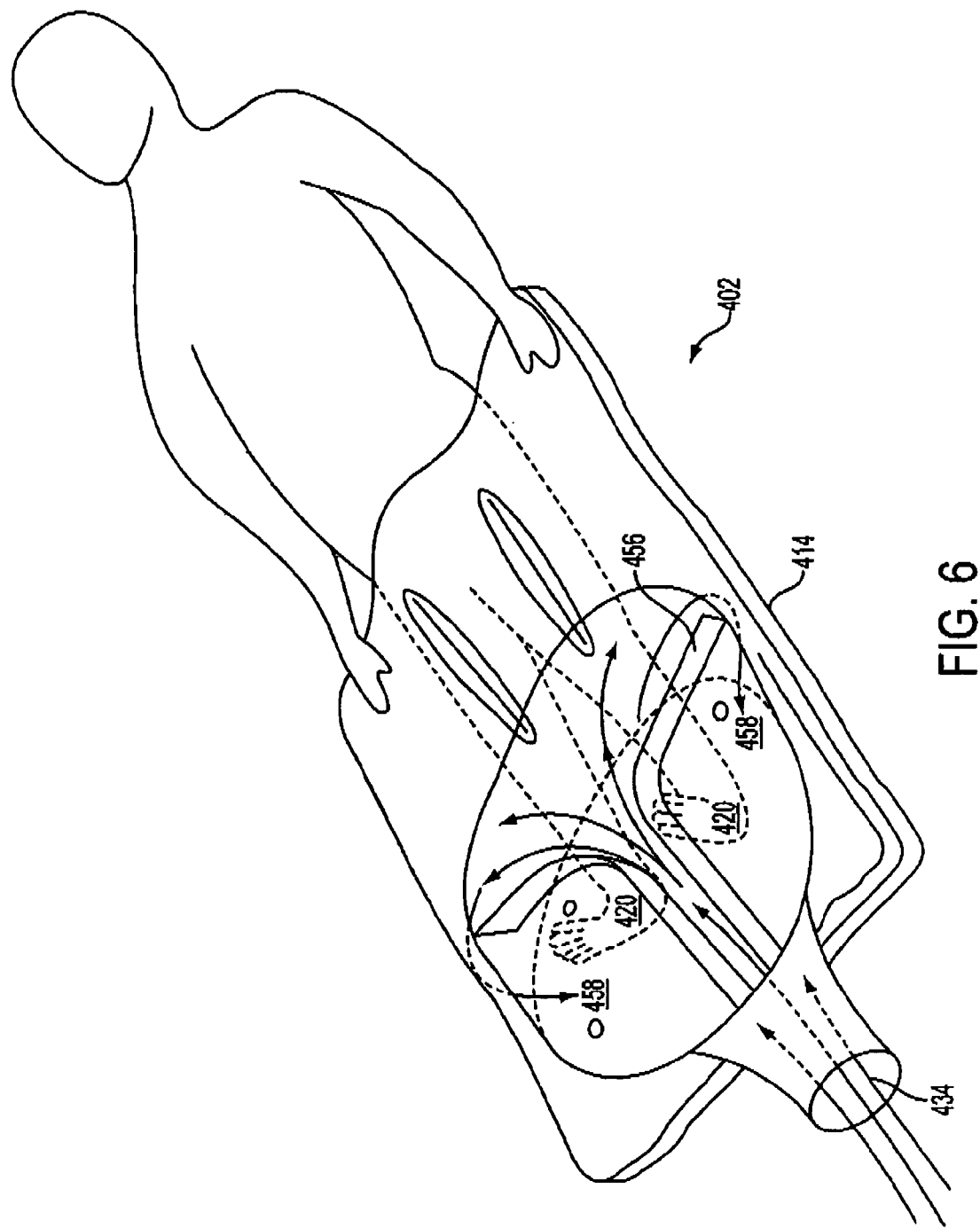
FIG. 6 shows a three-quarter view, partially cut-away, of an inflatable blanket for a forced air convection system according to a fourth embodiment of the invention.

In a fourth embodiment, shown in FIG. 6, inflatable blanket 402 has a pair of baffles 456 to reduce a flow 458 of inflation medium 434 proximate to the feet 420 of the patient 422. The location with reduced flow proximate to the feet 420 is a protected portion within the cavity of the blanket 402. If, e.g., inflation medium has the effect of raising or lowering a temperature of feet 420, it may be desirable to limit the flow of 458 of inflation medium 434 locally to feet 420, while allowing inflation medium 434 to circulate substantially freely in the remainder of inflatable blanket 402, in order to maintain a temperature of feet 420 at a comfortable level. The pair of baffles 456 may thus reduce the 'loft' in the area of blanket 402 proximate to feet 420 relative to that of the remainder of blanket 402. The pair of baffles 456 are representative of a restriction of a constriction. In a preferred embodiment, the pair of baffles 456 ends approximately 2 inches or 5.08 centimeters from peripheral edge 414. The pair of baffles 456 may further be, e.g. a controllable restriction, such that a range of rates of flow 458 of inflation medium 434 may be applied locally to feet 420. For instance, the pair of baffles 456 may adjustably or controllably block the flow from directly accessing a protected portion of the cavity while facilitating substantially free circulation to the remainder of the cavity.

Figure 7:
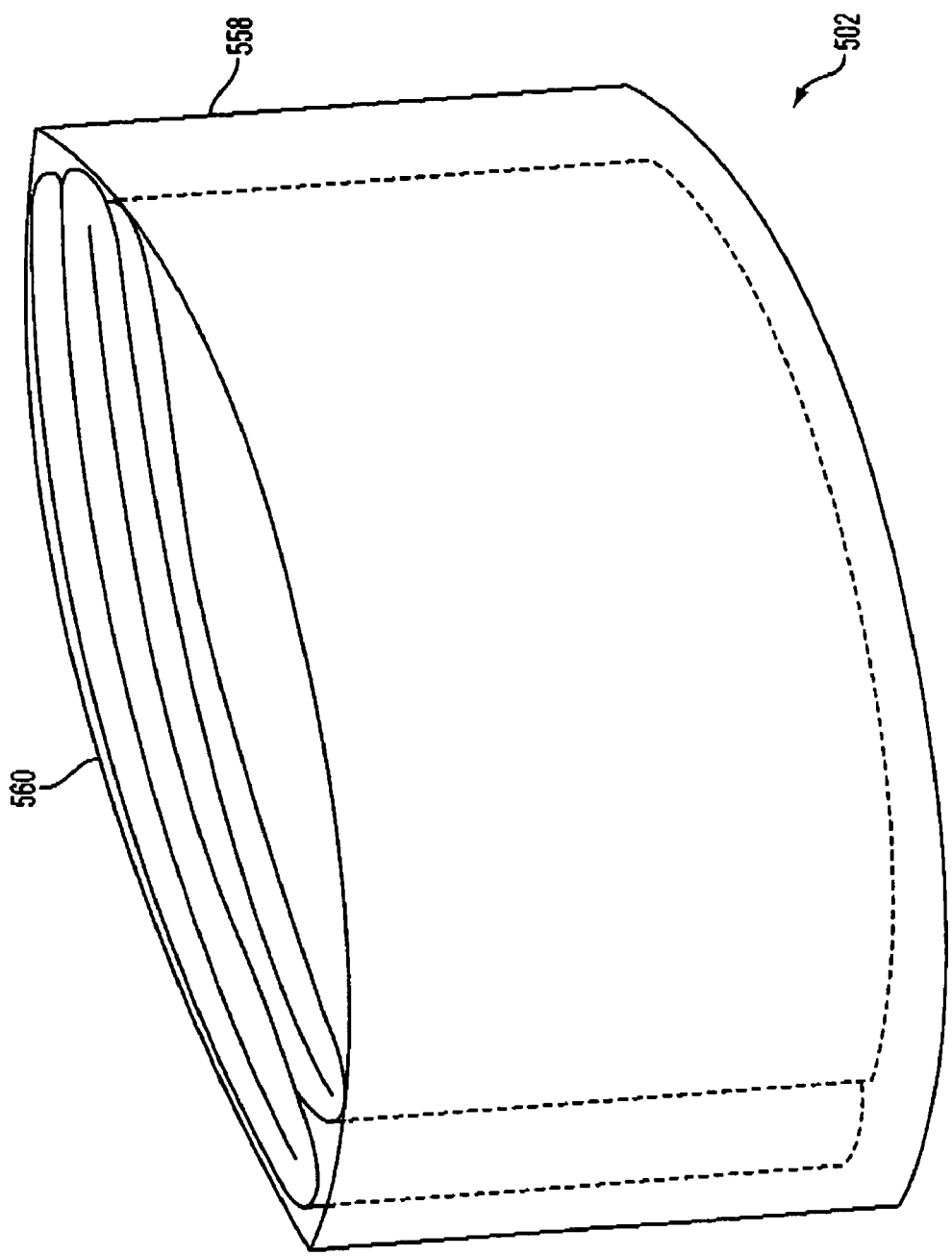
FIG. 7 shows an inflatable blanket for a forced air convection system according to a fifth embodiment of the invention.

In a fifth embodiment, shown in FIG. 7, inflatable blanket 502 is contained in a pouch 558 arranged around the blanket 502 before the inflation medium has been introduced to the blanket 502. Inflatable blanket 502 can thus be presented into a sterile field before pouch 558 is opened. In a preferred embodiment, pouch 558 has a tear-open opening 560. Tear-open opening 560 may be produced by, e.g. a line of perforations, or an adhesive or heat or plastic weld between the sides of pouch 558 which is weak in, e.g. shear or tension relative to the local shear or tensile strength of a parent material of pouch 558.

Figure 8:
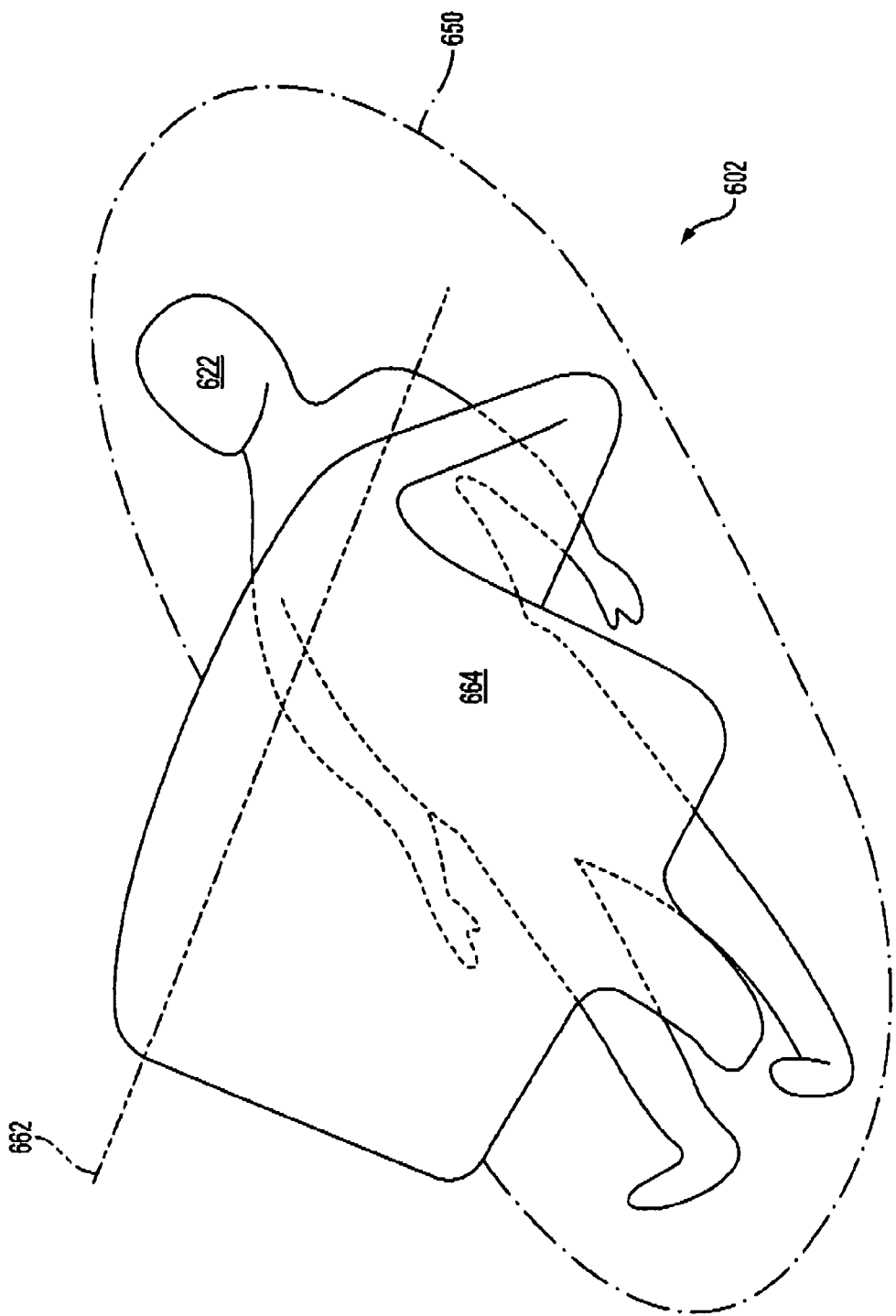
FIG. 8 shows an inflatable blanket for a forced air convection system according to a sixth embodiment of the invention.

In a sixth embodiment, shown in FIG. 8, inflatable blanket 602 has a fold 662 which allows the blanket 602 to open and allows placement over an abdomen 664 of the patient 622 before the inflation medium has been introduced to the blanket 602. In a preferred embodiment, blanket 602 opens downward without contaminating sterile field 650.

The inflatable blanket 602 may be used by tearing open pouch 558 containing the blanket in a folded condition, removing blanket 602 from the pouch 658, placing blanket 602 in the folded condition over a patient 622, opening blanket 602 down and out, and inflating the blanket 602.

While the invention has been described in detail above, the invention is not intended to be limited to the specific embodiments as described. It is evident that those skilled in the art may now make numerous uses and modifications of and departures from the specific embodiments described herein without departing from the inventive concepts. Zone Name: A1,AMD In a fourth embodiment, shown in FIG. 6, inflatable blanket 402 has a pair of baffles 456 to reduce a flow 458 of inflation medium 434 proximate to the feet 420 of the patient 422. The location with reduced flow proximate to the feet 420 is a protected portion within the cavity of the blanket 402. If, e.g., inflation medium has the effect of raising or lowering a temperature of feet 420, it may be desirable to limit the flow of 458 of inflation medium 434 locally to feet 420, while allowing inflation medium 434 to circulate substantially freely in the remainder of inflatable blanket 402, in order to maintain a temperature of feet 420 at a comfortable level. The pair of baffles 456 may thus reduce the 'loft' in the area of blanket 402 proximate to feet 420 relative to that of the remainder of blanket 402. The pair of baffles 456 are representatives of a restriction of a constriction. In a preferred embodiment, the pair of baffles 456 ends approximately 2 inches or 5.08 centimeters from peripheral edge 414. The pair of baffles 456 may further be, e.g. a controllable restriction, such that a range of rates of flow 458 of inflation medium 434 may be applied locally to feet 420. For instance, the pair of baffles 456 may adjustably or contollyably block the flow from directly accessing a protected portion of the cavity while facilitating substantially free circulation to the remainder of the cavity.

The invention claimed is:

1. A method, comprising:
   receiving a flow around an adjustable baffle and into a cavity of an inflatable blanket formed from a first layer and a second layer sealed together about a perimeter; and
   adjustably blocking the flow from directly accessing a protected portion of the cavity while facilitating substantially free circulation to a remainder of the cavity with the adjustable baffle.

2. The method of claim 1, comprising directing the flow away from feet of a patient properly disposed beneath the blanket.

3. The method of claim 1, comprising directing the flow about a circuitous path to reach the protected portion of the cavity.

4. The method of claim 1, comprising providing access from one side of the inflatable blanket to another side of the inflatable blanket via a slit through the inflatable blanket, wherein the perimeter of the slit is sealed to prevent flow loss.

5. The method of claim 1, comprising generating and heating the flow.

6. A method, comprising:
   connecting a receptacle of an inflatable blanket to a forced air source;
   covering a patient with the inflatable blanket; and
   adjusting a baffle disposed within the inflatable blanket proximate the receptacle to prevent a flow from the forced air source from directly circulating to a designated area within the inflatable blanket while facilitating substantially free circulation to a remainder of the inflatable blanket.

7. The method of claim 6, wherein the designated area is an area of the inflatable blanket proximate feet of the patient.

8. The method of claim 6, comprising opening a slit within the inflatable blanket by separating a separable seal line disposed proximate a leg artery of the patient.

9. A method, comprising:
   receiving a flow into a narrow portion of a pair of adjustable baffles disposed within a cavity of an inflatable blanket; and
   directing the flow along a length of the adjustable baffles and expelling the flow from a widened portion between the adjustable baffles into the cavity of an inflatable blanket, wherein the cavity is formed from a first layer and a second layer sealed together about a perimeter.

10. The method of claim 9, comprising adjustably blocking the flow from directly accessing a protected portion of the cavity with the adjustable baffles while facilitating substantially free circulation to a remainder of the cavity.

11. The method of claim 9, comprising generating and heating the flow.

12. A method, comprising:
   receiving a flow into a pair of adjustable baffles disposed within a cavity of an inflatable blanket;
   directing the flow along a length of the adjustable baffles;
   cooling the flow;
   expelling the flow from a widened portion between the adjustable baffles into the cavity of an inflatable blanket, wherein the cavity is defined by a first layer and a second layer sealed together about a perimeter.

13. The method of claim 12, comprising expelling the flow at a point within the cavity beyond a patient's feet when the patient is properly positioned beneath the blanket.

14. The inflatable blanket of claim 13, comprising generating and heating the flow prior to receiving the flow into the adjustable baffles.

\* \* \* \* \*